United States Patent [19]

Hirsch

[11] 4,290,771

[45] Sep. 22, 1981

[54] DIAGNOSTIC AGENT FOR THE DETECTION OF UROBILINOGEN

[75] Inventor: Wolfgang Hirsch, Wunstorf, Fed. Rep. of Germany

[73] Assignee: Behringwerke Aktiengesellschaft, Marburg an der Lahn, Fed. Rep. of Germany

[21] Appl. No.: 74,748

[22] Filed: Sep. 12, 1979

[30] Foreign Application Priority Data

Sep. 14, 1978 [DE] Fed. Rep. of Germany ....... 2839931

[51] Int. Cl.³ .......................................... G01N 33/72
[52] U.S. Cl. .................... 23/230 B; 23/929; 252/408
[58] Field of Search ................... 23/230 B, DIG. 929; 422/56; 252/408

[56] References Cited

U.S. PATENT DOCUMENTS 3,850,576 11/1974 Rittersdorf et al. .............. 422/56 X

FOREIGN PATENT DOCUMENTS 2531539 1/1977 Fed. Rep. of Germany ........ 422/56

Primary Examiner—Michael S. Marcus
Attorney, Agent, or Firm—Curtis, Morris & Safford

[57] ABSTRACT

Diagnostic agent for the detection of urobilinogen in body liquids, which comprises an absorption carrier which is impregnated with a diazonium salt, the sum of the Hammett-sigma values of all substituents of the diazonium salt being greater than $+0.4$.

4 Claims, No Drawings

DIAGNOSTIC AGENT FOR THE DETECTION OF UROBILINOGEN

The present invention relates to a diagnostic agent for the detection of urobilinogen in liquids, preferably in biological liquids, in particular in the urine.

It is known to detect urobilinogen with a solution of dimethylaminobenzaldehyde in hydrochloric acid. This detection, known as the Ehrlich reaction, has gained considerable importance in medicinal diagnostics in the course of time, although it is not very specific. At present, the detection of urobilinogen in the urine is considered the standard method for the diagnosis of liver and gall diseases.

In view of the expanding use of rapid diagnostics, test papers for the detection of urobilinogen on the basis of the Ehrlich reaction have been developed. But these papers, too, imply the non-specificity of the Ehrlich test and, furthermore, they have the disadvantage that the color reaction develops very slowly.

It has already been described as early as 1907 (dissertation by Karl Thomas, Freiburg) that urobilinogen also reacts with diazotized amines. But, this so-called yellow diazo reaction has not found acceptance in medicinal laboratories. In recent times, however, test papers for the detection of urobilinogen in liquids based on the diazo reaction have been proposed (DE-PS 21 30 559, DE-OS 22 29 611, DE-OS 23 64 844). As reagents, aromatically substituted or anellated stable phenyl-, pyrrole- and pyrazolediazonium salts are described (DE-OS 22 29 611) or also substituted benzidine derivatives have been used (DE-OS 23 64 844). Another patent (DE-PS 21 30 559) describes the use of stable benzene-diazonium salts, which contain in the ortho- or para-position at least one polyatomic, electron donor group which is capable of mesomerism, the sum of the Hammett sigma values of all substituents not exceeding the value +0.4. Moreover, it has also been found that an aromatic diazonium compound with a sum of the sigma values of the substituents of +0.77 gives a usable reagent for the detection of urobilinogen (DE-AS 25 21 402). However, upon reworking it has been found that the compound indicated therein is obviously unstable and is present essentially in a substituted form in the mixture of reagents ready for use. In addition, a compound enters into the detection reaction in which the sum of the Hammet sigma values is smaller than +0.4. Therefore, it was not to be expected that compounds with a sum of the Hammett sigma values of the substituents greater than +0.4 would lead to usable reagents for the detection of urobilinogen.

The test papers based on the diazo reaction are in general less liable to perturbations than the papers based on the Ehrlich reaction. The papers known hitherto frequently show a reaction with bilirubin, a bile dyestuff which occurs in the urine in the case of gall and liver diseases.

Now, we have found that, surprisingly, there exist aromatic diazonium salts with a sum of the Hammett values of the substituents of over +0.4, which are stable and extremely suitable for the detection of urobilinogen.

In particular, we have found that the compounds of the general formula I are specific and sensitive agents for proving urobilinogen and yield a reliable proof of urobilinogen even in the presence of bilirubin.

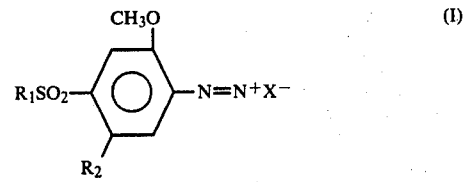

In the formula I $R_1$ represents $CH_3-$, $C_2H_5-$, $CH_2=CH-$, $HOCH_2CH_2-$ or $CH_3OC_2H_5-$ radical, $R_2$ represents hydrogen or a $C_1-C_4$-alkyl radical, and $X^-$ represents a stabilizing anion.

$X^-$ may be, preferably, a chloride, sulfate, tetrafluoroborate, hexafluoroantimonate, hexafluoroantimonysulfonate, trifluormethylsulfonate, arylsulfonate or carboxylic acid radical.

Diazonium salts of the formulas I are particularly suitable for use on an absorptive carrier, optionally in admixture with one or several solid acids and/or a stabilizer and/or a wetting agent and/or an optical brightener.

The compounds of the invention react with urobilinogen within a few seconds to red dyestuffs. The color reaction is not disturbed by the natural substances contained in the urine, for example urine indicane and urea. The compounds of the invention do not react with bilirubin either so that even if bilirubin and urobilinogen are present at the same time, the latter can be proved specifically.

This is especially surprising as it is recommended in the DE-AS 21 30 559, column 4, lines 26–29, that in order to suppress the reaction with bilirubin, a diazonium salt with relatively low electrophily should be used. In contradistinction to this recommendation, with the diazonium compounds of the invention with relatively high electrophily, a high specificity is reached even if both substances are present at the same time. The Hammett sigma values of the compounds of the formula I are +0.72 if $R_2$=hydrogen and +0.65 to +0.62, if $R_2=C_1-C_4$-alkyl radical. For the $CH_2=CH-SO_2$ group in the 4-position, no values can be found in the literature; however, an additional electrophilic effect toward the β-hydroxyethylsulfonyl group is to be expected.

The compounds of the formula I are preferably used for the preparation of test papers. For this purpose, they are applied on an absorptive carrier, together with an acid and optionally with additives such as stabilizers, wetting agents and optical brighteners.

For preparing them, an absorptive carrier, preferably paper or a polyester fleece, is impregnated with a solution of the above-mentioned reagents in a mixture of an organic water-miscible solvent and water and then dried in agitated air at temperatures between 0° and 80° C.

The diazonium compounds of the formula I, which are added in quantities of from 0.02 to 2 g, preferably 0.1 to 0.5 g/100 ml, to the impregnating solution, may be prepared according to the usual methods of diazo chemistry or they are prepared in the impregnating solution from the corresponding amine (4-methyl-sulfonyl-2-methoxyaniline according to DE-OS 21 14 578 and 2-methoxy-5-methyl-4-(β-hydroxyethyl)-sulfonyl-aniline according to DE-AS 11 50 163, Example 1) according to methods known in diazo chemistry.

Solid acids, which are added in quantities of from 1-30 g, preferably 5-15 g/100 ml, to the impregnating solution, may be organic aromatic and aliphatic carboxylic or sulfonic acids, either alone or in admixture with one another or with inorganic acids. Stabilizers such as naphthalene-(1,5)-disulfonic acid disodium salt or sodium lauryl sulfate, are well known from diazo chemistry. They may be added to the impregnating solution in quantities ranging from 1 to 10 g, preferably from 1 to 7 g/100 ml.

Wetting agents such as dodecylbenzenesulfonic acid or sodium laurylsulfate may be added to the impregnating solution in quantities of from 0.1 to 5 g, preferably from 0.5 to 1 g/100 ml.

Optical brighteners, which improve the readability, may be added in quantities of from 0.01 to 5 g, preferably 0.2 to 2 g/100 ml to the impregnating solution. As such, stilbene derivatives such as those designated Blankophor ® traded by Bayer AG may be used.

As the solvent, water in admixture with a water-miscible organic solvent, preferably a lower alcohol, for example methanol, may be used, the ratio of water to solvent being not critical but is determined only by the solubility of the components.

As absorptive carriers, filter papers but also fleeces from polyamide or polyester or other acid-resistant plastics materials may be used. The material of the absorbing carrier is, however, not critical. Even other materials which are capable of absorbing the impregnating solution may be used. The individual components of the formulation may, of course, be applied successively onto the carrier material, if this be required by the solubility or special circumstances.

The compounds of the formula I may also be used for detection in solution. For this purpose, a solution is prepared according to the above-described procedure, into which the solution to be tested is suitably injected. In this case, the use of an optical brightener is not necessary. Reading is effected either by comparison with a color scale or with a spectral photometer.

For carrying out the process of the invention, the diagnostic agents prepared according to the above-described method are shortly dipped into the liquid to be tested. After a few seconds, the change of color can be read, optionally by comparison with a color scale.

The diagnostic agent of the present invention is illustrated in more detail in the following Examples:

Filter paper Schleicher & Schüll, 2316 is impregnated with each one of the solutions indicated in Examples 1 and 2 and dried at room temperature.

EXAMPLE 1:

| | |
|---|---|
| 4-Methylsulfonyl-2-methoxybenzene-diazoniumtetrafluoroborate | 0.1 g |
| Methanol | 10 ml |
| meta-phosphoric acid | 10 g |
| Citric acid-1-hydrate | 3 g |
| Dodecylbenzene sulfonic acid | 1 g |
| Water | ca. 100 ml |

The test paper prepared according to this Example shows 0.5 mg of urobilinogen/100 ml solution and gives with urobilinogen-containing urine a red coloration.

Test papers can be prepared in the same manner using each time 0.1 g of the following diazonium compounds:
4-Ethylsulfonyl-2-methoxybenzenediazoniumtrifluoromethylsulfonate
4-Vinylsulfonyl-2-methoxybenzenediazoniumtetrafluoroborate
4-(β-Hydroxyethyl)sulfonyl-2-methoxybenzenediazoniumtetrafluoroborate
4-(Methoxyethyl)sulfonyl-2-methoxybenzenediazoniumarylsulfonate
4-Methylsulfonyl-2-methoxy-5-methyl-benzenediazoniumtetrafluoroborate
4-Ethylsulfonyl-2-methoxy-5-methyl-benzenediazoniumtetrafluoroborate
4-Vinylsulfonyl-2-methoxy-5-methyl-benzenediazoniumtetrafluoroborate
4-(β-Hydroxyethyl)sulfonyl-2-methoxy-5-methyl-benzenediazoniumtetrafluoroborate
4-(Methoxyethyl)sulfonyl-2-methoxy-5-methyl-benzenediazoniumtetrafluoroborate.

The test papers obtained likewise show a red coloration with urobilinogen-containing urine.

EXAMPLE 2

10 g of meta-Phosphoric acid
3 g of citric acid-1-hydrate
1 g of naphthalene-(1,5)-disulfonic acid disodium salt
1 g of dodecylbenzenesulfonic acid
1 g of optical brightener are dissolved in
90 ml of distilled water, cooled to 4°-5° C. and combined with a suspension of
0.15 g of 4-(β-hydroxyethyl)-sulfonyl-2-methoxy-5-methyl aniline in
10 ml of methanol. Subsequently, about 2 ml of isoamylnitrile are added.

The filter paper is impregnated with this solution and after drying it may be used for the detection of urobilinogen.

A filter paper prepared according to this Example shows after immersion into normal urine, depending on its content of urobilinogen, a weakly pink coloration. With urine having a high content of urobilinogen, red to deep red colorations are obtained.

The same colorations, although somewhat more yellowish owing to the present bilirubin, are obtained with papers according to Examples 1 and 2, when adding to the urine samples prior to the test each time 10 mg of bilirubin/100 ml of solution. On the other hand, the test agents show with urobilinogen-free but bilirubin-containing urine no color reaction within comparable times. While no coloration can be observed after 5 minutes, a green coloration may develop after 10 minutes.

In the same manner, test papers can be prepared using each time 0.15 g of the following aniline compounds:
4-Methylsulfonyl-2-methoxy-aniline
4-Ethylsulfonyl-2-methoxy-aniline
4-Vinylsulfonyl-2-methoxy-aniline
4-(β-Hydroxyethyl)sulfonyl-2-methoxy-aniline
4-(Methoxyethyl)sulfonyl-2-methoxy-aniline
4-Methylsulfonyl-2-methoxy-5-methyl-aniline
4-Ethylsulfonyl-2-methoxy-5-methyl-aniline
4-Vinylsulfonyl-2-methoxy-5-methyl-aniline
4-(Methoxyethyl)sulfonyl-2-methoxy-5-methyl-aniline The test papers obtained likewise develop a red coloration with urobilinogen-containing urine and show no color reaction with urobilinogen-free but bilirubin-containing urine.

What is claimed is:
1. A method for the detection of urobilinogen which comprises contacting a sample suspected of containing urobilinogen with a diagnostic agent containing an effective amount of a compound having the formula

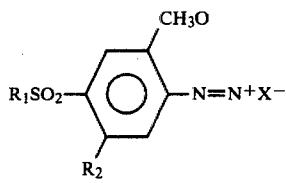

wherein $R_1$ is selected from the group of radicals consisting of $CH_3-$, $C_2H_5-$, $CH_2=CH-$, $HOC_2H_5-$ and $CH_3OC_2H_5-$, $R_2$ is hydrogen or a $(C_1-C_4)$-radical, and $X^-$ is a stabilizing anion.

2. The method of claim 1 wherein $X^-$ is selected from the group consisting of chloride, sulfate, tetrafluoroborate, hexafluoroantimonate, hexafluoroantimony sulfonate, trifluoromethylsulfonate, arylsulfonate and carboxylic acid radicals.

3. The method of claims 1 or 2 wherein the sum of the Hammett sigma values for all substituents is greater than +0.4.

4. The method of claims 1 or 2 wherein the sum of the Hammett sigma values for all substituents is greater than +0.6.

* * * * *